United States Patent [19]

Green

[11] Patent Number: 5,116,353
[45] Date of Patent: May 26, 1992

[54] SAFETY TROCAR

[75] Inventor: David T. Green, Westport, Conn.

[73] Assignee: United States Surgical Corporation, Norwalk, Conn.

[21] Appl. No.: 593,676

[22] Filed: Oct. 5, 1990

[51] Int. Cl.[5] .............................................. A61B 17/32
[52] U.S. Cl. .................................... 606/184; 604/164; 30/366
[58] Field of Search ............... 604/160, 161, 164, 165, 604/168, 169, 185, 188, 246, 247, 248, 264, 272, 274, 283, 51; 606/184, 185; 128/751, 752, 753, 754; 30/151, 152, 162, 368, 367, 366

[56] References Cited

U.S. PATENT DOCUMENTS

| | | |
|---|---|---|
| 1,213,001 | 1/1917 | Philips . |
| 2,496,111 | 2/1950 | Turkel . |
| 2,623,521 | 12/1952 | Shaw . |
| 3,030,959 | 4/1962 | Grunert . |
| 3,605,744 | 6/1971 | Dwyer . |
| 3,643,649 | 2/1972 | Amato . |
| 3,657,812 | 4/1972 | Lee . |
| 3,882,849 | 3/1974 | Jamshidi . |
| 4,018,228 | 2/1975 | Goosen . |
| 4,210,146 | 7/1980 | Banko . |
| 4,220,155 | 9/1980 | Kimberling et al. . |
| 4,254,762 | 1/1981 | Yoon . |
| 4,299,230 | 11/1981 | Kubota . |
| 4,356,826 | 11/1982 | Kubota . |
| 4,375,815 | 3/1983 | Burns . |
| 4,393,587 | 7/1983 | Kloosterman . |
| 4,411,653 | 10/1983 | Razi . |
| 4,414,974 | 11/1983 | Dotson et al. . |
| 4,499,898 | 2/1985 | Knepshield et al. . |
| 4,535,773 | 8/1985 | Yoon . |
| 4,556,059 | 12/1985 | Adamson, Jr. . |
| 4,559,041 | 12/1985 | Razi . |
| 4,601,710 | 7/1986 | Moll . |
| 4,637,393 | 1/1987 | Ray . |
| 4,654,030 | 3/1987 | Moll et al. . |
| 4,723,545 | 2/1988 | Nixon et al. . |
| 4,730,613 | 3/1988 | Gordy . |
| 4,733,662 | 3/1988 | DeSatnick et al. . |
| 4,813,940 | 3/1989 | Parry . |

FOREIGN PATENT DOCUMENTS

| | | |
|---|---|---|
| 350291 | 1/1990 | European Pat. Off. . |
| 836392 | 4/1952 | Fed. Rep. of Germany . |
| 344853 | 8/1972 | U.S.S.R. . |
| 537677 | 1/1977 | U.S.S.R. . |
| 921554 | 4/1982 | U.S.S.R. . |

OTHER PUBLICATIONS

F. S. Zubairov—"Needle for the Puncture and Lavage of the Abdominal Cavity" (Russian with English Translation).

*Primary Examiner*—C. Fred Rosenbaum
*Assistant Examiner*—William Lewis

[57] ABSTRACT

A safety trocar is provided in which the cutting tip is withdrawn into the cannula in response to counterforce being removed from the cutting tip, e.g., by the tip entering a body cavity. The cutting tip is maintained in the exposed positioned by a mechanism associated with the oburator shaft, and is automatically withdrawn into the cannula under the force of a spring when the first mechanism is released by a second mechanism associated with the oburator. Penetration force is maintained at a minimum and safe and efficacious trocar entry is facilitated.

20 Claims, 11 Drawing Sheets

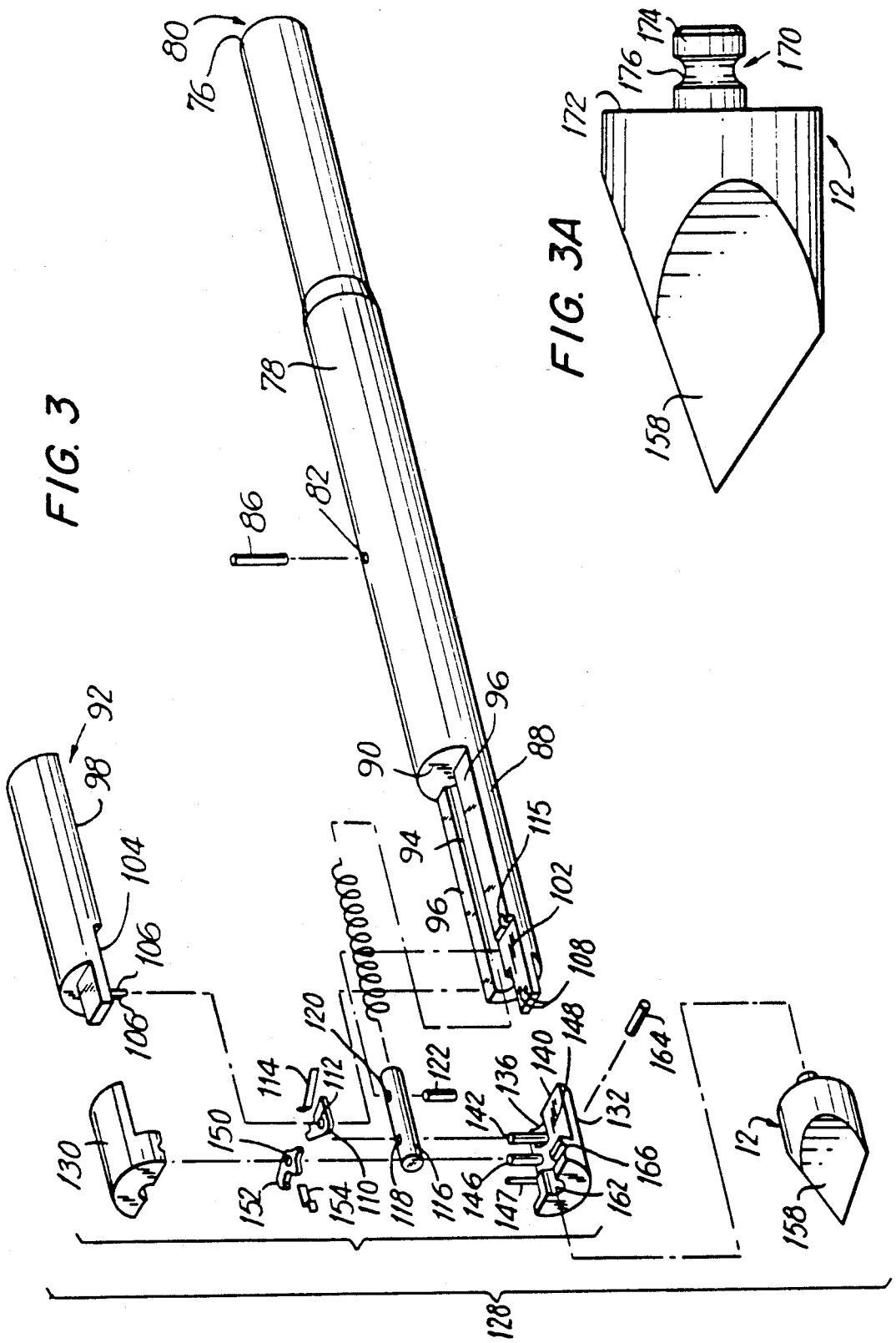

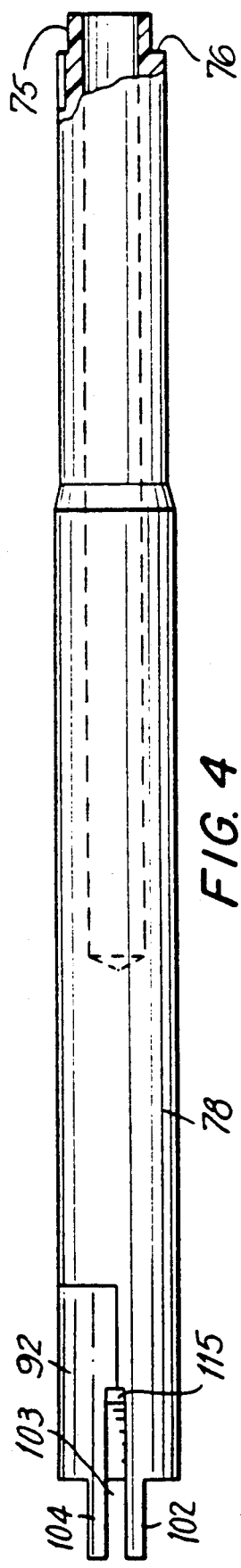
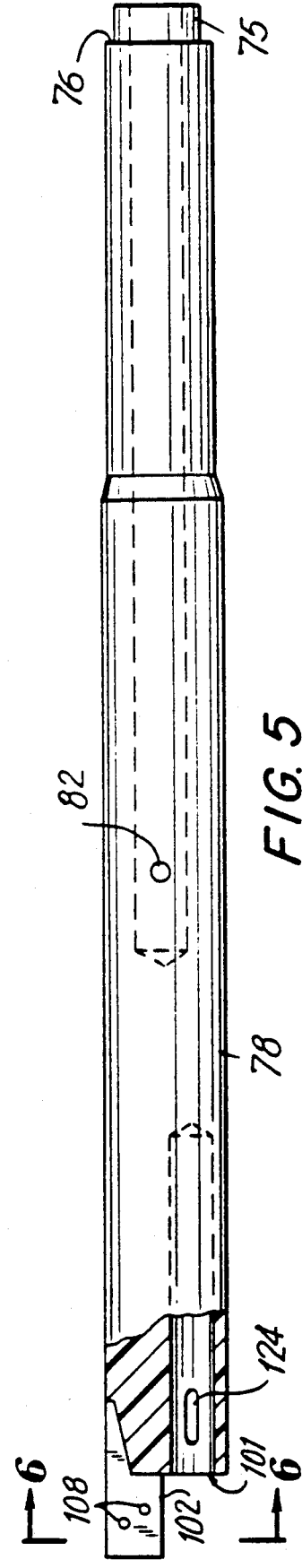
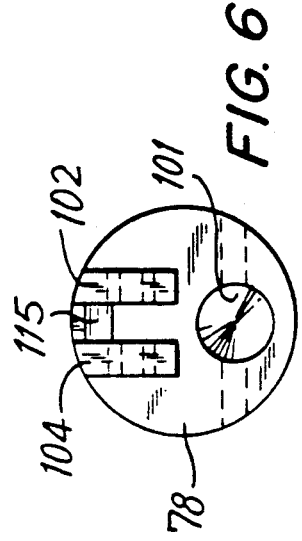

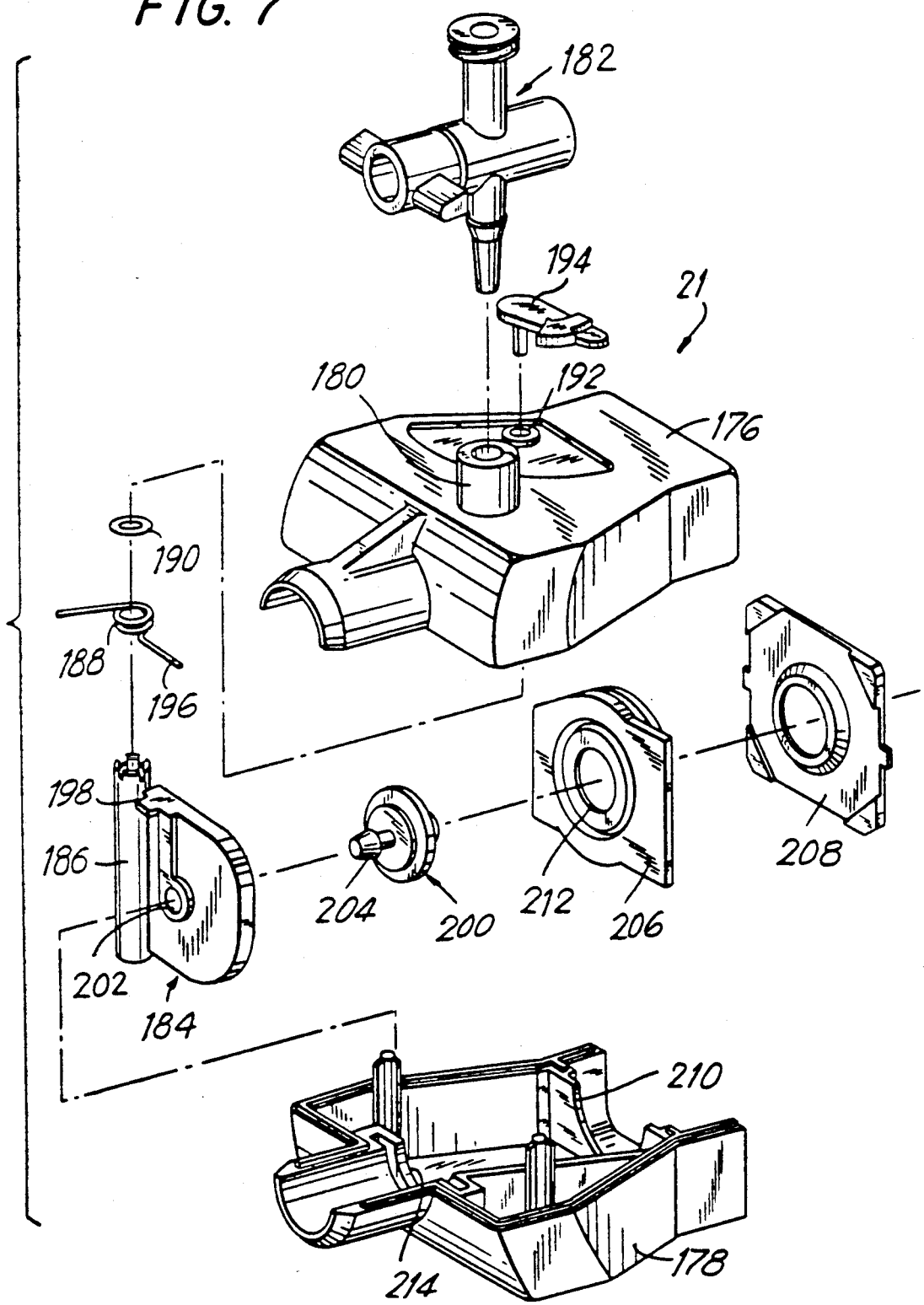

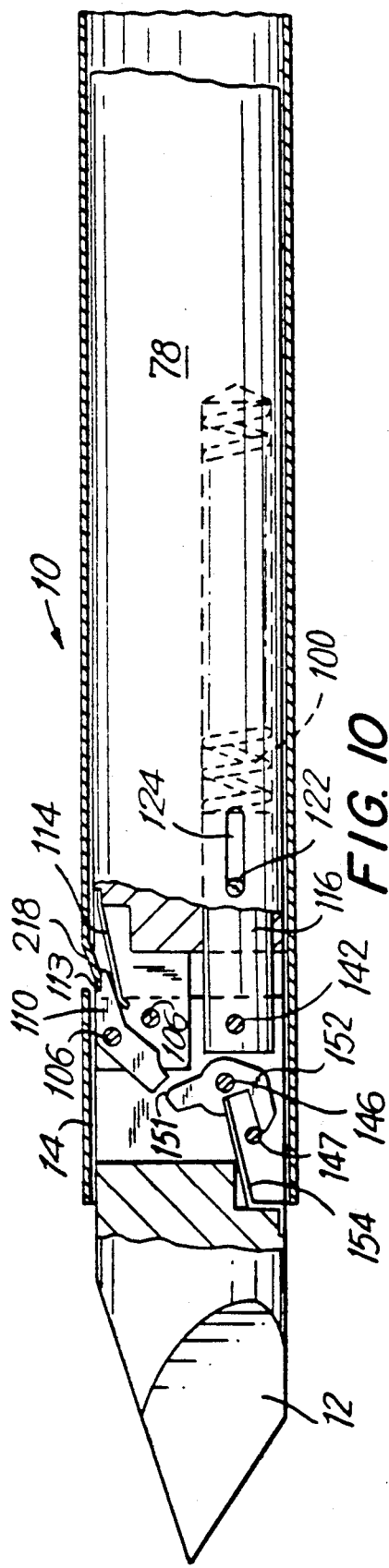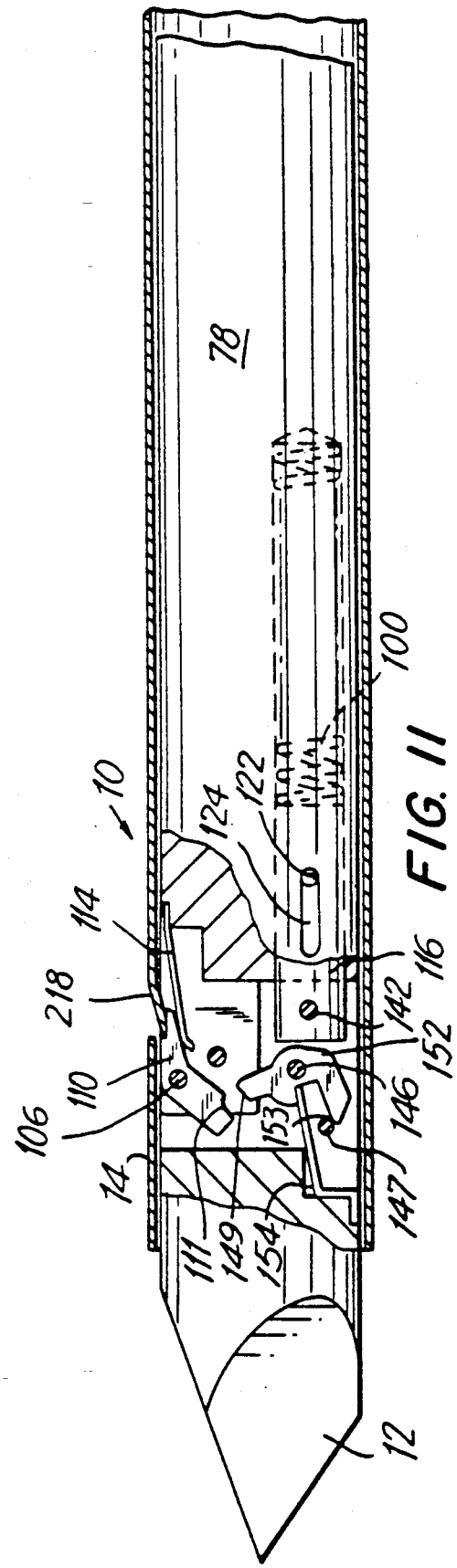

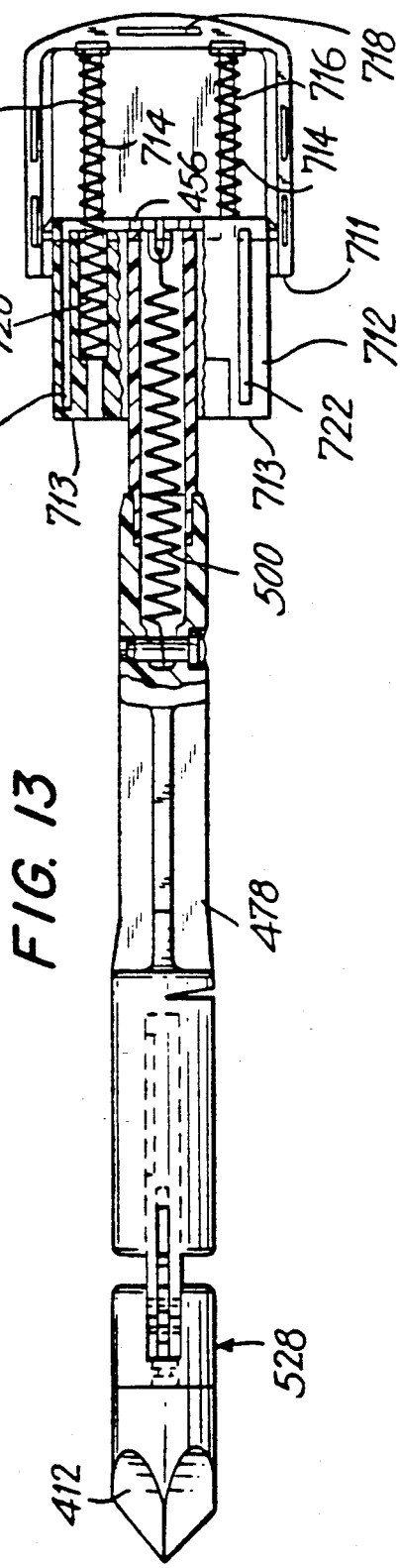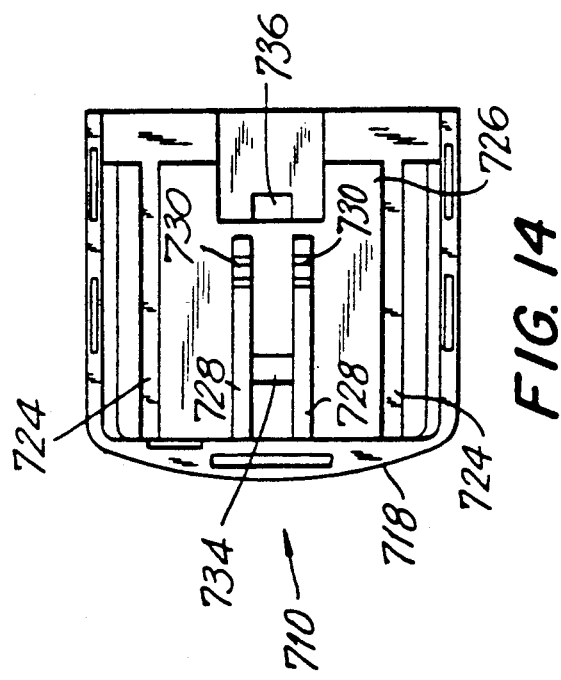

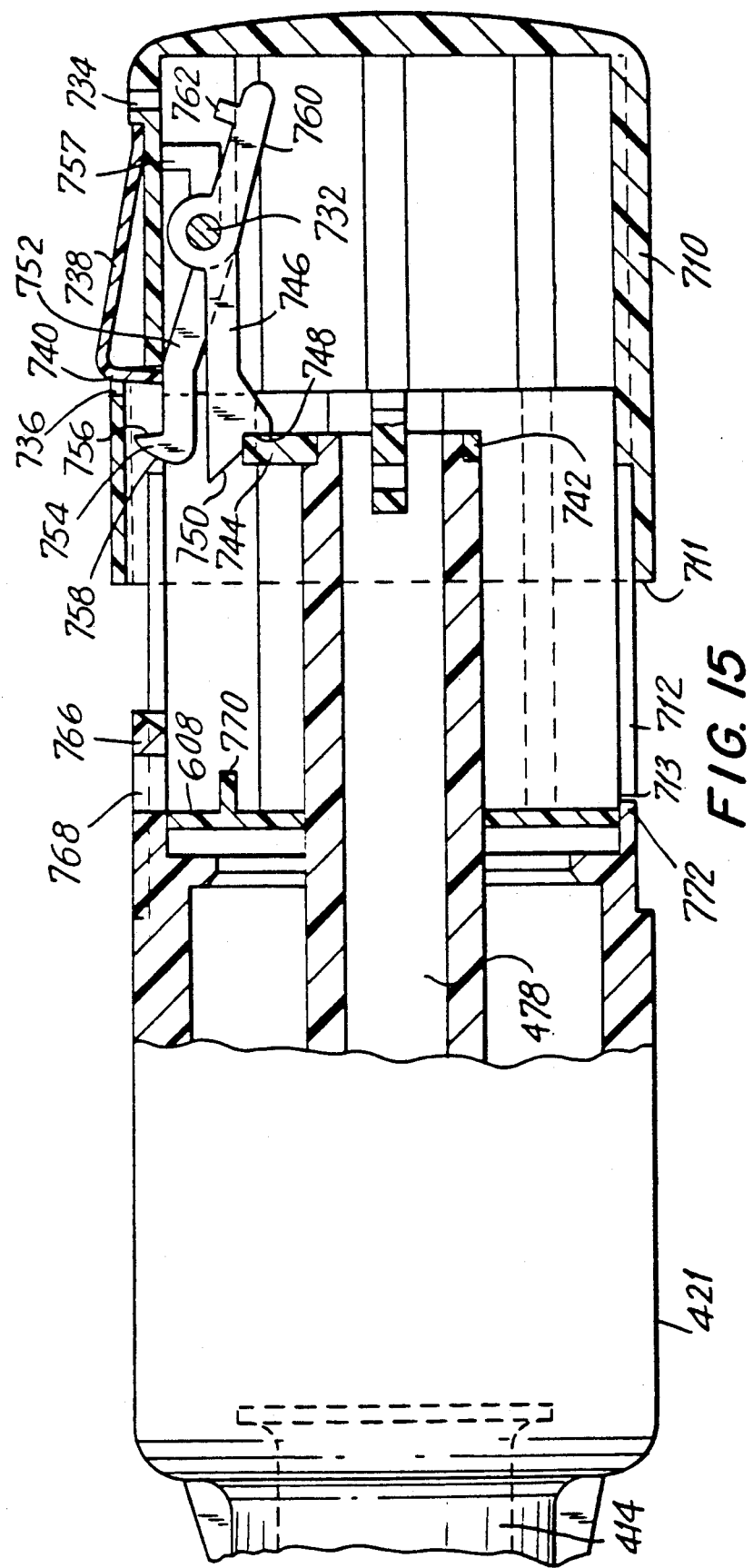

SAFETY TROCAR

TECHNICAL FIELD

This invention relates to a surgical trocar and more particularly to a safety trocar in which the sharp cutting tip retracts into the cannula so as to minimize the likelihood of inadvertent injury to viscera and other internal tissue.

DESCRIPTION OF THE PRIOR ART

Trocars are sharp pointed surgical instruments used to puncture a body cavity. Trocars are generally adapted to be used together with a tubular trocar sleeve or cannula. Once the body cavity has been punctured by the trocar, the sharp trocar is removed from the cannula, thereby leaving the cannula extending into the body cavity. Endoscopic surgical procedures are then performed through the cannula with accessory instrumentation such as laparoscopes, dissectors, graspers, etc.

Commercially available safety trocars include a spring-loaded safety shield which is adapted to cover the trocar tip once the body cavity has been entered so as to provide an increased level of protection to internal structures from puncture or laceration. For example, U.S. Pat. No. 4,601,710 to Moll describes a trocar assembly which consists of two subassemblies: a trocar subassembly which includes a sharp-tipped trocar and a spring-loaded tubular safety shield positioned therearound, and a cannula subassembly. When ready for use, the trocar and safety shield of the trocar subassembly are inserted through the cannula. The safety shield is initially in its distal-most position covering the trocar tip. Exertion of pressure against the skin with the trocar causes the shield to be pushed rearwardly against the spring to expose the piercing tip of the trocar. The tip penetrates the skin and underlying tissue with continued pressure. Once the tip has penetrated through the wall and has entered the cavity, the force against the front end of the shield ceases and the shield is automatically moved back to its distally extended position. Viscera and other internal tissue are thus protected from contact with the sharp piercing tip and potential damage therefrom.

U.S. Pat. No. 4,535,773 to Yoon suggests several alternative safety trocar designs. In one embodiment (see FIGS. 22-28), a spring-loaded blunt probe is provided within the trocar shaft, as with conventional Verres needles. The blunt probe is adapted to reciprocally slide through an aperture in the trocar tip such that when the trocar tip enters a body cavity, the blunt probe springs distally forward through the aperture to prevent contact between the trocar tip and body organs. In a second embodiment (see FIGS. 33-36), pressure sensors or transducers are fitted into the trocar blade surfaces and the distal end of the cannula. Sets of electrical leads run through the trocar shaft and communicate with an alarm network in the proximal portion of the device. A further modification is suggested in which the trocar shaft is initially manually extended and maintained in its extended position by a detent which protrudes through a hole in the surrounding tubular structure. The hole aligns with a solenoid socket. When the instrument is fully assembled and the trocar tip is forced through a body wall, the electrical leads running through the trocar shaft send electrical signals to the solenoid which, at the appropriate instant, forces the detent from the hole, allowing the trocar tip to withdraw into the cannula. Additional mechanisms for effecting withdrawal of cutting implements are also known. See, e.g., U.S. Pat. Nos. 4,375,815 to Burns; 3,657,812 to Lee; and 3,030,959 to Grunert.

SUMMARY OF THE INVENTION

It has now been found that an improved safety trocar may be provided which includes:

(a) a cannula assembly comprising a cannula and a cannula housing;

(b) a trocar assembly comprising a sharp trocar tip, an obturator shaft, and a trocar housing;

(c) means associated with the obturator shaft which releasably maintains the trocar tip in an extended position;

(d) means for releasing the releasable obturator means; and (e) biasing means for retracting the trocar tip from the extended position to a retracted position in response to release of the releasable obturator means.

The safety trocar of the present invention is adapted to be armed by the surgeon immediately prior to use. Arming may be accomplished by advancing a finger which extends through the trocar housing, by compressing the trocar housing toward the cannula housing, or by like means. Once armed, the trocar tip releasably protrudes beyond the distal end of the cannula.

As the surgeon presses the trocar, and more particularly the trocar tip, against the body wall of a patient, the initial counterforce exerted by the body wall against the trocar tip causes a mechanism associated with the obturator shaft to position the obturator shaft (together with the cutting tip) for immediate retraction upon entering the body cavity. Thus, removal of the counterforce from the trocar tip, e.g., upon entering the body cavity, results in immediate and automatic withdrawal of the trocar tip into the cannula under the force of a biasing means, e.g., a spring.

In a preferred embodiment of the trocar, the trocar tip is mounted to an extension member which is reciprocally mounted to and biased away from the obturator shaft. A latch is associated with the obturator shaft, the latch being biased radially outward and being adapted to engage an internal shelf formed in the cannula when the trocar is armed. A pawl is associated with the extension member which, upon exertion of a counterforce against the trocar tip, is positioned and biased to release the latch from engagement with the cannula shelf. Upon the trocar tip entering the body cavity, the pawl contacts and releases the latch from engagement with the cannula shelf. A spring which was loaded upon arming the trocar is thus free to immediately retract the trocar tip into the cannula.

The trocar of the invention is also designed to permit manual retraction or disarming of the cutting tip, if so desired. This is accomplished by permitting the trocar housing to be manually rotated with respect to the cannula housing, thereby disengaging the latch from the cannula shelf. The trocar is also typically provided with an indicator which signals the surgeon as to whether the trocar is armed or disarmed. For example, the relative position of the finger used to arm the trocar may be calibrated or indexed to communicate the trocar tip position or a window may be provided through which a trocar tip position indicator is visible.

In one embodiment of the invention, the trocar housing comprises two interconnected housing bodies. The two housing bodies are adapted to reciprocate with respect to each other and preferably nest one within the other. A mechanism is associated with the two housings which permits the trocar tip to be armed by compressing the two housings such that they assume a nested configuration. One or both of the trocar housings preferably latch to the cannula housing when in this nested position. A mechanism for manually releasing the trocar housings from the nested configuration is also typically provided.

The trocar of the present invention provides a safe and efficacious means for gaining access to body cavities to permit minimally-invasive diagnostic and surgical procedures to be accomplished. The trocar is equipped with a reliable mechanism for effectuating immediate, automatic retraction of the cutting tip into the cannula. Penetration force is kept to a minimum through the unique internal mechanism for releasably maintaining the trocar tip in the armed position.

BRIEF DESCRIPTION OF THE DRAWINGS

The present invention will become apparent from the following detailed description taken in conjunction with the accompanying drawings in which:

FIG. 3 is an exploded view of the distal portion of the trocar assembly;

FIG. 3A is a side view of the cutting tip;

FIG. 4 is a side view, partially in cross section, of a middle portion of the trocar assembly;

FIG. 5 is a bottom view, partially in cross section, of a middle portion of the trocar assembly;

FIG. 6 is a front view of a middle portion of the trocar assembly;

FIG. 7 is an exploded view of the proximal portion of the cannula assembly;

FIG. 10 is a sectional side view of the trocar with the trocar tip in its advanced position;

FIG. 11 is a sectional side view of the trocar with the trocar tip advanced, but with a counterforce (not pictured) applied thereto;

FIG. 13 is a sectional top view of the alternate trocar assembly;

FIG. 14 is a sectional bottom view of the alternate trocar housing;

FIG. 15 is a sectional side view of the proximal portion of the alternate embodiment;

DETAILED DESCRIPTION OF THE INVENTION

Figure 1:
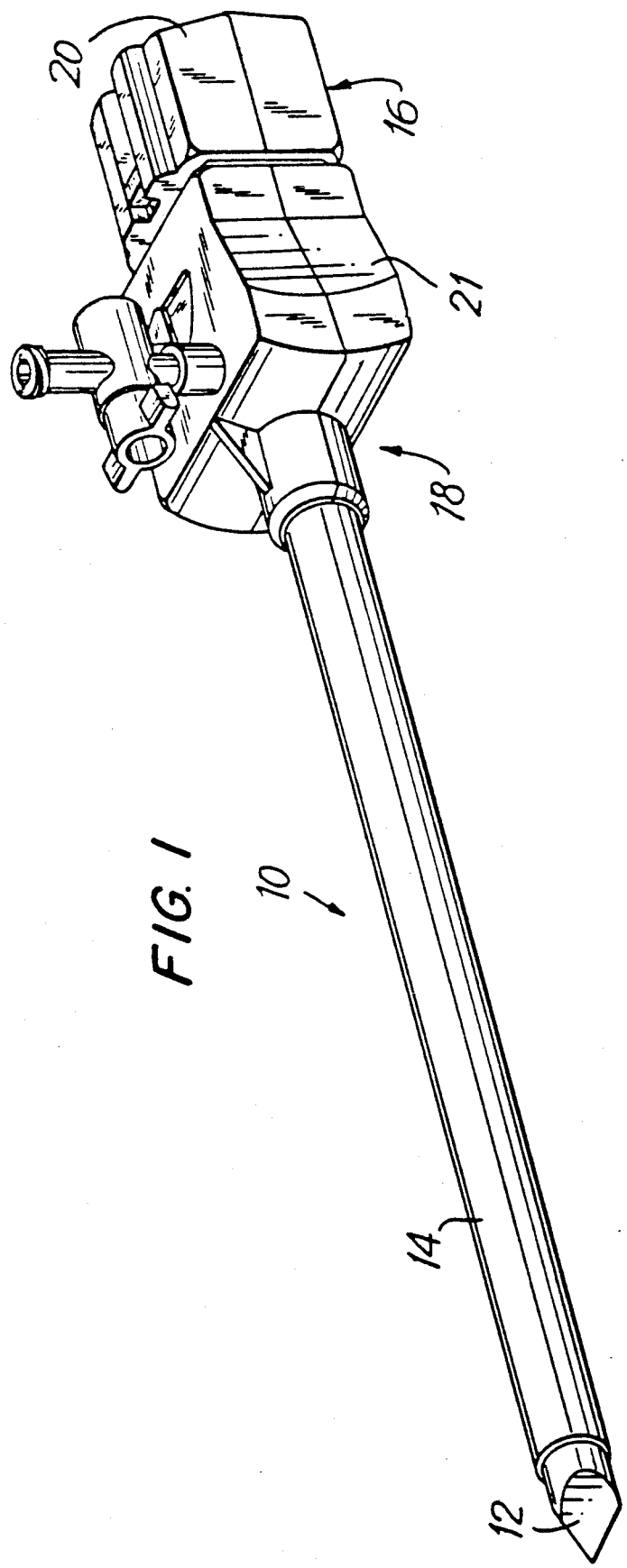
FIG. 1 is a side perspective view of a trocar of the present invention.

Referring to FIG. 1, trocar 10 is shown in its fully assembled condition with cutting tip 12 extending from cannula 14. Trocar 10 includes a trocar assembly 16 and a cannula assembly 18. The longitudinally extending or endoscopic portion of trocar assembly 16 which extends from trocar housing 20 is shielded from view in FIG. 1 by cannula housing 21 and cannula 14, except for extended cutting tip 12.

Figure 2:
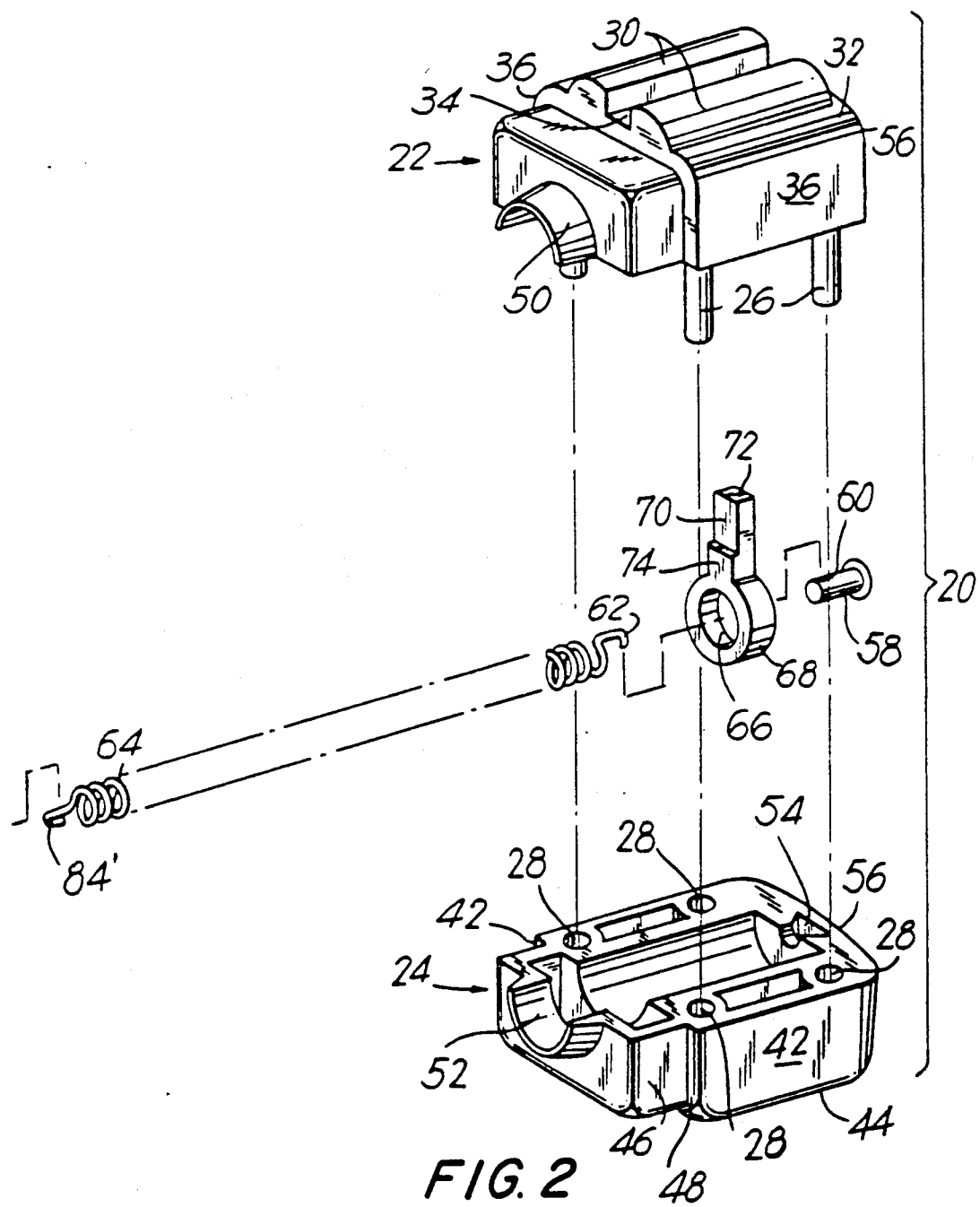
FIG. 2 is an exploded view of the proximal portion of the trocar assembly of the trocar of FIG. 1.

Referring now to FIGS. 1 and 2, trocar assembly 16 includes trocar housing 20 which comprises upper housing 22 and lower housing 24. Upper housing 24 includes four mounting legs 26 which are adapted to fit within corresponding apertures 28 in lower housing 24. Upper housing 22 also includes two longitudinally extending, parallelly spaced, semi-hemispheric projections 30 which face upward from top face 32 of upper housing 22. Semi-hemispheric projections 30 surround an axial slot 34 formed in top face 32, the function of which will be described hereinbelow.

Side faces 36 and upper face 32 of upper housing 22 step down to form a substantially rectangular distal projection 38 and substantially U-shaped abutment face 40. Side faces 42 and bottom face 44 of lower housing 24 also step down to form a corresponding substantially rectangular distal projection 46 and a substantially U-shaped abutment face 48. Extending distally from rectangular projections 38 and 46 are semi-circular extensions 50 and 52, respectively. Thus, when upper housing 22 and lower housing 24 are joined to form trocar housing 20, a tubular path is formed into trocar housing 20.

An anchor socket 54 is formed in the rear walls 56 of upper and lower housing 22 and 24 which receives anchor pin 58. Aperture 60 in pin 58 receives the proximal end 62 of tension spring 64. Tension spring 64 extends through tubular passageway 66 in ring 68. Finger 70 extends upwardly from ring 68 and is adapted to reciprocally slide within slot 34 in upper housing 22. The length of finger 70 is preferably selected such that its upper face 72 extends to a height equal to or less than the height of the upper faces of semi-hemispheric projections 30. Thus, when a surgeon grasps trocar housing 20, movement of finger 70 within axial slot 34 is unimpeded by the surgeon's hand. Semi-hemispheric projections 30 may take many shapes and configurations, provided free movement of finger 70 within slot 34 is ensured. Ring 68 also forms a distally directed face 74 which fits around proximally extending tubular projection 75 (see FIG. 4), and abuts and is fixedly secured, e.g., by an adhesive, to rear face 76 of obturator shaft 78.

Referring to FIGS. 3 to 6, obturator shaft 78 includes an internal bore 80 which begins at rear face 76 and extends to a point distal of aperture 82. Tension spring 64 extends through bore 80 and hook 84 which is formed on the distal end of tension spring 64 is retained by pin 86 which extends through aperture 82 in obturator shaft 78 and a matching aperture on the opposite face of shaft 78. When mounted within bore 80, tension spring 64 fixedly joins obturator shaft 78 to trocar housing 20, subject to the extension and retraction of tension spring 64.

At its distal end, obturator shaft 78 forms a hemispheric distally extending arm 88 and a substantially semi-circular abutment face 90. A corresponding hemispheric tubular body 92 is adapted to mount onto hemispheric arm 88 to provide a tubular body of substantially identical cross-section as the proximal end of obturator shaft 78. A semi-circular channel 94 is formed in the top face 96 of hemispheric arm 88. Channel 94 extends to abutment face 90 at its proximal end. A corresponding semi-circular channel is formed in the lower face 98 of hemispheric body 92. Compression spring 100 fits within the tubular bore 101 formed by channel 94 and the corresponding channel in hemispheric body 92.

A downwardly extending shoulder 102 is formed on top face 96 of hemispheric arm 88 and a corresponding upwardly extending shoulder 104 is formed in lower face 98 of hemispheric body 92. Thus, when hemispheric body 92 is mounted on hemispheric arm along upper face 96 and lower face 98, e.g., by adhesives, sonic welding or the like, a slot 103 is formed between shoulders 102 and 104. Two staggered pins 106 extend downwardly from shoulder 104 and two corresponding staggered apertures 108 are formed in shoulder 102. The radially outwardly positioned pin 106 passes through an aperture 112 in latch 110 before entering the radially outward aperture 108. The other pin 106 passes directly into the corresponding aperture 108 and serves to align hemispheric body 92 with obturator shaft 78. As discussed in more detail below, latch spring 114 is positioned within the slot 103 formed between shoulders 102 and 104, nests at its proximal end into a slot 115 formed in upper face 96, and biases latch 110.

Cylindrical rod 116 includes two axially spaced apertures 118 and 120 and is dimensioned to ride within tubular channel. A pin 122 fits within aperture 120 and extends radially outward into slots 124 formed in arm 88 (see FIG. 5) and hemispheric member 92. Proximal face 126 of rod 116 abuts the distal end of compression spring 100.

Extension tip 128 is made up of substantially hemispheric upper and lower tip members 130 and 132, respectively. Semicircular channels 134 and 136 extend into the proximal faces 138 and 140 of upper and lower tip members 130 and 132, respectively. Upwardly extending pin 142 is mounted in semicircular channel 136, extends upward through aperture 118 in rod 116, and passes into an aperture (not shown) in the bottom face 144 of upper tip member 130. A second upwardly extending pin 146 extends from the upper face 148 of lower tip member 132 through an aperture 150 in pawl 152 and into an aperture (not shown) in the bottom face 144 of upper tip member 144. A leaf spring 154 is positioned adjacent pawl 152 and biases pawl 152 in a manner discussed in more detail below. A third upwardly extending pin 147 provides a rotational stop to pawl 152, as is also discussed hereinbelow.

A pyramidal cutting tip 12 having three blade surfaces 158 is rotatably mounted into upper and lower tip members 130 and 132 by way of matching semicircular collars 160 and 162. Pin 164 passes through a channel formed by semicircular passages 166 and 168 in upper and lower tip members 130 and 132. As shown in FIG. 3A, a proximally extending rod 170 extends from the rear face 172 of cutting tip 12 which forms a flange 174 at its proximal end. A radial channel 176 is formed between the rear face 172 and flange 174 into which pin 164 extends. Pin 164 thus locks tip 156 into upper and lower tip members 130 and 132 while permitting rotational movement with respect thereto.

Turning to FIG. 7, cannula housing 21 comprises upper cannula housing body 176 and lower cannula housing body 178. A tubular port 180 is formed on upper cannula body 176 which receives stopcock assembly 182. A flapper valve support body 184 is pivotally mounted within cannula housing 21 with the lower end of support leg 186 seating into lower cannula body 178 and the upper end passing through a helically wound torsion spring 188, an O-ring 190, an aperture 192 in upper cannula body 176, and into cooperation with an external lever 194. The transverse leg 196 of torsion spring is positioned below lip 198 which extends from the upper portion of flapper valve support body 184. Self-seating flapper valve 200 mounts onto flapper valve support body 184 through cooperation between aperture 202 in support body 184 and distally extending mounting rod 204 on flapper valve 200. A seal member 206 and stabilizer plate 208 are mounted into cannula housing 21, e.g., with an adhesive, in cooperation with internal mating flanges 210 within upper and lower cannula housings 176 and 178. Seal member 206 includes a gasket 212 which forms a gas seal with flapper valve 200 when flapper valve support body 184 is pivoted into a substantially parallel relation with seal member 206. A second set of internal mating flanges 214 are provided toward the distal end of upper and lower cannula housings 176 and 178 to receive flange 216 formed at the proximal end of cannula 14 (see FIG. 8).

Figure 8:
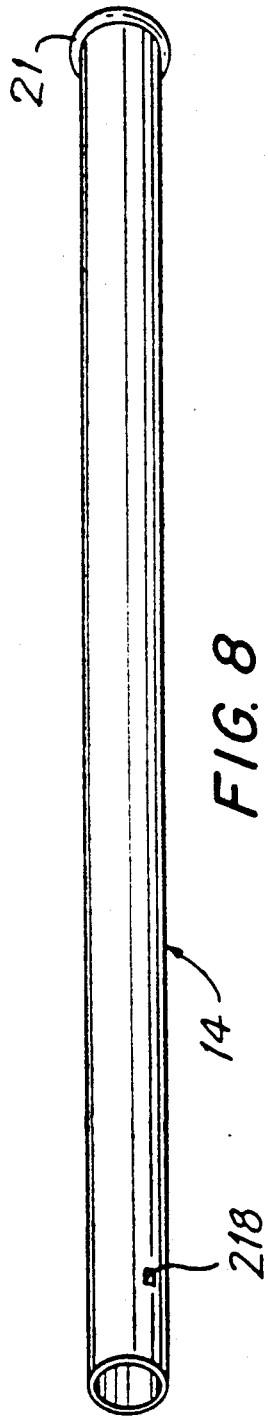
FIG. 8 is a side perspective view of the distal portion of the cannula assembly.

Referring to FIG. 8, cannula 14 is a hollow tubular member having a flange 216 at its proximal end and an internal shelf 218 formed toward its distal end. Internal shelf 218 is formed by inwardly notching or lancing tubular cannula 14 at the desired location. Cannula 14 is preferably fabricated from stainless steel or a radiolucent material, as for example, fiberglass.

The length of cannula 14 is selected such that when trocar 10 is fully assembled, as shown in FIG. 1, trocar tip 12 is shielded by cannula 14 when the tip is retracted, but trocar tip 12 is fully exposed from cannula 14 when in its advanced position. Cannula 14 may be manufactured with various internal diameters, the most common internal diameters being 5, 10 and 12 millimeters.

In use, the surgeon inserts trocar tip 12 and obturator 78 of trocar assembly 16 into cannula housing 21. Contact with trocar tip 12 pivots flapper valve support body 184 so as to provide free passage for trocar tip 12 and obturator 78 into cannula 14. Alternatively, flapper valve support body 184 may be manually pivoted using lever 194. As obturator 78 enters cannula housing 21, a gas seal is provided therewith by gasket 212. The surgeon continues to advance the endoscopic portion of trocar assembly 16 into cannula housing 21 until the front face of trocar housing 20 abuts the rear face of cannula housing 21.

Figure 9:
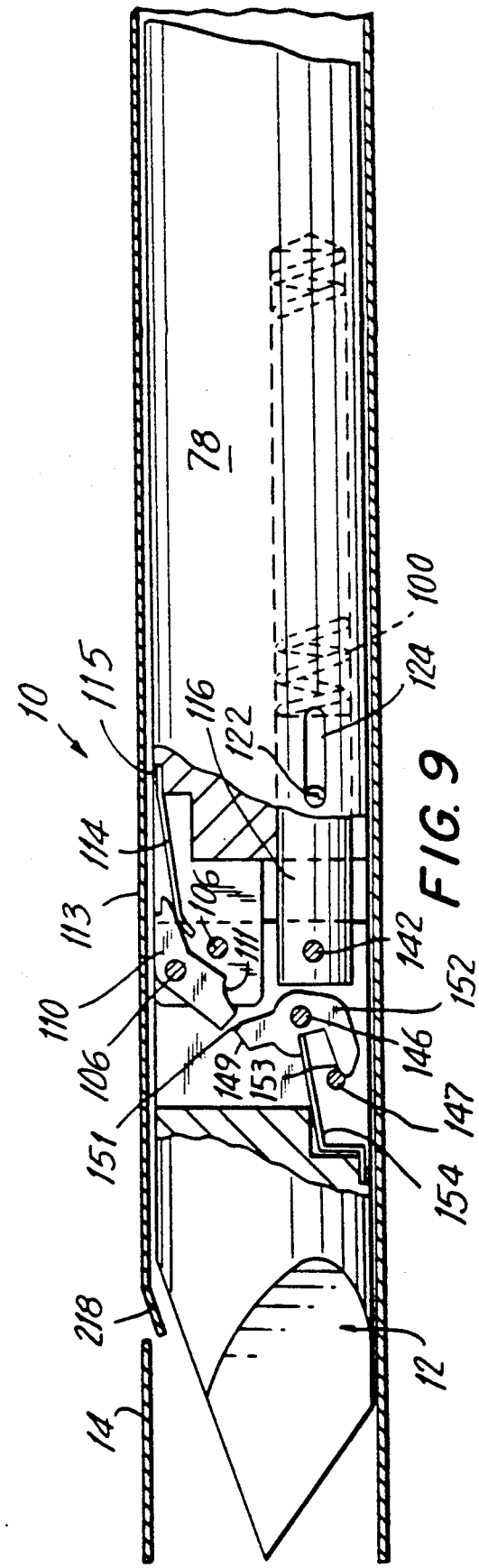
FIG. 9 is a sectional side view of the trocar with the trocar tip in its retracted position.

Referring to FIG. 9, the initial positions of the internal mechanisms of trocar 10 are shown. In this initial position, trocar tip 12 is within cannula 14. Latch 110 is biased radially outward against the inner wall of cannula 14 by latch spring 114. In other words, latch spring 114 biases latch 110 counterclockwise around pin 106 into engagement with the inner wall of cannula 14. Pawl 152 is biased clockwise by leaf spring 154 around pin 146. Stop pin 147 prevents further clockwise motion of pawl 152 through contact with leg 153. Pin 122 is shown in its distal-most position within slots 124. As such, compression spring 100 is unloaded.

When the surgeon is ready to use trocar 10, finger 70 is advanced distally within axial slot 34 in trocar housing 20. Through contact between ring 68 and obturator shaft 78, distal movement of finger 70 also advances obturator shaft 78 and trocar tip 12 distally, thereby exposing trocar tip 12 from cannula 14. Distal movement of obturator shaft 78 also places spring 64 in tension, thereby biasing obturator shaft 78 and trocar tip 12 proximally, i.e., to a position in which trocar tip 12 is shielded within cannula 14. As shown in FIG. 10, however, such proximal motion is prevented by contact between engagement surface 113 of latch 110 and internal shelf 218 in cannula 14. Latch spring 114 biases latch 110 into engagement with internal shelf 218.

With the trocar tip 12 advanced (as shown in FIG. 1), the surgeon presses trocar 10 against a patient's body wall. As is apparent from FIG. 3, extension tip 128 (to which trocar tip 12 is mounted) is mounted to obturator 78 by rod 116. Inasmuch as rod 116 is secured to obturator 78 by pin 122 which rides in slots 124, the initial counterforce imparted by the body wall against trocar tip 12 causes pin 122 to move proximally within slots 124, thereby loading compression spring 100. As extension tip 128 moves proximally, rearward face 151 of pawl 152 contacts the forward face of latch 110. Inasmuch as latch 110 is fixed against internal shelf 218 by the combined loads of tension spring 64 and leaf spring 110, contact between latch 110 and pawl 152 causes pawl 152 to rotate counterclockwise against the bias of leaf spring 154 so as to gain clearance thereby. As soon as pawl 152 passes proximally past latch 110, leaf spring 154 causes pawl 152 to return clockwise to its rest position against stop pin 147, as shown in FIG. 10.

As trocar tip 12 enters the body cavity, the counterforce applied against trocar tip 12 by the body wall ceases. The absence of counterforce allows compression spring 100 to spring distally, advancing pin 122 from its proximal-most position in slot 124 (FIG. 11) to its distal-most position (FIGS. 9 and 10). Rod 116 is also advanced distally, thereby separating extension tip 128 from obturator 78. As extension tip 128 moves distally, upper inclined surface 149 on pawl 152 contacts abutment face 111 on latch 110. Inasmuch as further clockwise rotation of pawl 152 is prevented by stop pin 147, contact between upper inclined surface 149 and abutment face 111 as pawl 152 moves distally causes latch 110 to rotate clockwise around pin 106 against the bias of latch spring 114. This clockwise rotation of latch 110 results in clockwise rotation of engagement surface 113 which frees engagement surface 113 from engagement with internal shelf 218.

As soon as engagement surface 113 clears internal shelf 218, there no longer remains any restraint to the return of tension spring 64 to its unloaded condition. Thus, finger 70, obturator 78 and cutting tip 12 move proximally under the return force of tension spring 64. Trocar 10 therefore assumes the initial position shown in FIG. 9 with trocar tip 12 within cannula 14, extension tip 128 separated from obturator 78, and pawl 152 distal of latch 110.

If desired, a surgeon may re-advance trocar tip 12 by repeating the steps outlined above as, for example, if trocar tip 12 retracts before complete entry into the body cavity. It is also possible for a surgeon to manually retract trocar tip 12 if, for example, it is determined that trocar insertion is inadvisable or to be delayed after trocar tip 12 has been advanced. Manual retraction may be accomplished by rotating trocar housing 20 with respect to cannula housing 21. This rotational motion serves to move latch 110 off of internal shelf 218, thereby freeing tension spring 68 to withdraw trocar tip 12 into cannula 14. To facilitate such manual retraction, means for providing a clearance between the rear face of cannula housing 21 and the front face of trocar housing 20 may be provided. For example, means may be associated with finger 70 which is adapted to abut stabilizer plate 208 when cutting tip 12 is advanced, and which can be further advanced so as to force cannula housing 21 away from trocar housing 20, as for example, by advancing finger 70 in further slot means on the top face 32 of trocar housing 20. Such clearance means is preferably spring biased in the proximal direction so as to require a conscious effort to provide a clearance between cannula housing 21 and trocar housing 20.

Turning to FIGS. 12 to 15, an alternative embodiment of the trocar assembly of the present invention is shown. Trocar assembly 416 includes trocar housing 420, obturator 478, and cutting tip 412. The latch/pawl mechanism at the distal end of trocar assembly 416 is substantially the same as that described in connection with trocar assembly 16 (see FIGS. 2-12). However, in this alternate embodiment, proximally extending rod 570 which extends from the rear face 572 of trocar tip 412 is reciprocally mounted in a socket 700 in tip extension 528.

In addition, rod 516 which joins extension tip 528 to obturator 478 exhibits a substantially L-shape which is defined by base 702 and axial leg 704. Spring 500 fits within a tubular bore 101 which opens into a distal receiving chamber 706 which is dimensioned to receive base 702 of rod 516. The axial length of receiving chamber 706 defines the distance over which rod 516 may travel in response to a counterforce being applied to cutting tip 412. The L-shape of rod 516 serves to stabilize rod 516 and prevent rotation of extension tip 528 relative to obturator 478.

Turning to the proximal end of trocar assembly 416, trocar housing 420 comprises an outer housing 710 and an inner housing 712 reciprocally mounted therein. Tension spring 500 is fixed at its proximal end to anchor 454 which extends distally from the rear face 456 of inner housing 712.

Referring to FIG. 13, two compression springs 714 are provided within outer housing 710. Compression springs 714 are mounted to rear wall 718 of outer housing 710 and extend into bores 720 which are formed in the rear face 456 of inner housing 712 and extend into the body thereof. Preferably, anti-kink rods 716 are included within compression springs 714 to prevent kinking as compression springs 714 expand and retract, the length of anti-kink rods 716 being such that proximal travel of inner housing is not retarded thereby. Guide rails 722 are formed on the top and bottom surfaces of inner housing 712 to facilitate reciprocal motion with respect to outer housing 710.

Turning to FIG. 14, a sectional bottom view of outer housing 710 is provided. Guide tracks 724 are formed in top face 726 which correspond to and guide longitudinal movement of guide rails 722. Two support arms 728 are also formed in top face 726, support arms 728 defining transversely aligned, concave forks 730. Concave forks 730 are adapted to receive pin 732, as discussed below. A viewing window 734 and release window 736 are also formed in top face 726.

Returning to FIG. 12 and additionally referring to FIG. 15, release leaf spring 738 is mounted, e.g., by an adhesive, atop face 726, the hook region 740 of which extends through release window 736. A flange 742 with upwardly extending finger 744 is formed at the proximal end of obturator 478. An obturator pusher arm 746 is pivotally mounted to outer housing 710 by pin 732 which is received in forks 730. Pusher arm 746 defines an abutment face 748 and an inclined cam surface 750 at its distal end and block projection 751 at its proximal end. Abutment face 748 engages finger 744 of flange 742.

Also mounted to outer housing 710 by pin 732 is housing latch finger 752. Housing latch finger 752 includes upwardly directed hook 754 which defines latch face 756 and distally directed cam surface 758. Downwardly directed inclined face 760 and upwardly directed indicator tab 762 are formed at the proximal end of latch finger 752. Indicator tab 762 is dimensioned to be received by viewing window 734.

A helically wound torsion spring 764 is mounted on pin 732 between pusher arm 746 and housing latch finger 752. Torsion spring 764 cooperates with the aforesaid members to bias the proximal ends of pusher arm 746 and housing latch finger 752 away from each other. Thus, block projection 751 is biased by torsion spring 764 into contact with outer housing 710 and abutment face 748 is biased into engagement with finger 744.

Figure 16:
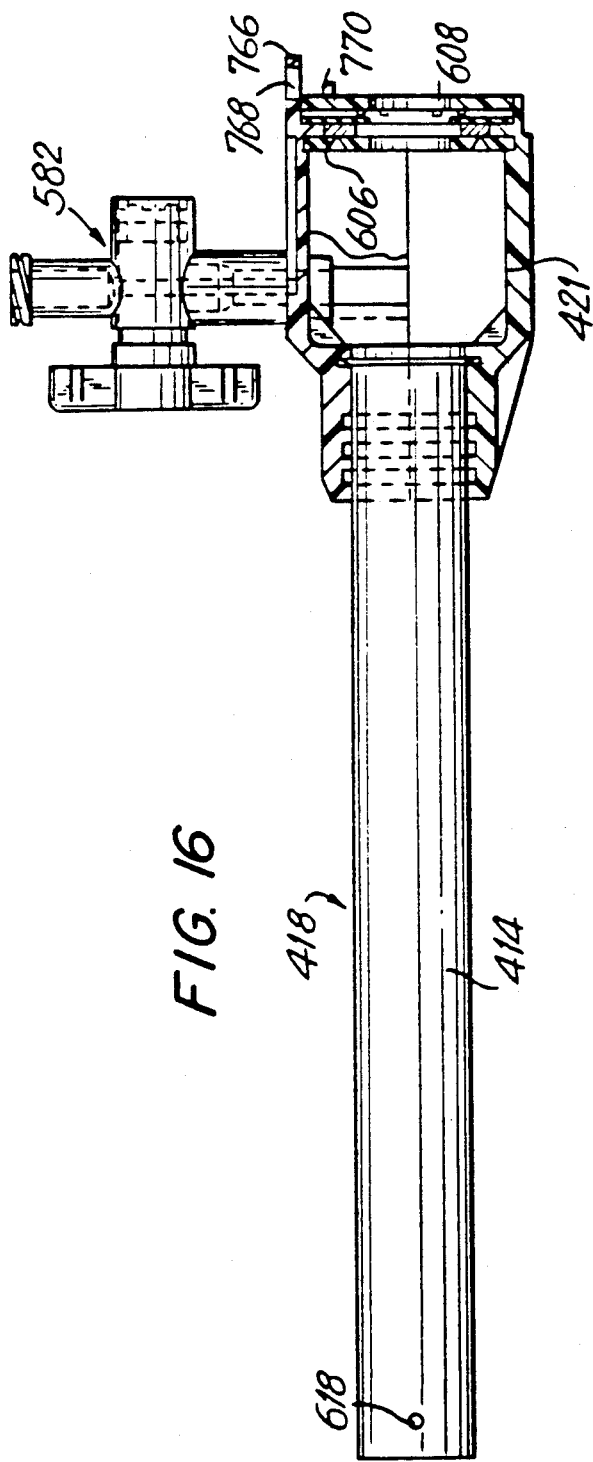
FIG. 16 is a sectional side view of an alternate cannula assembly.

Referring to FIGS. 15 and 16, cannula assembly 418 of this alternate embodiment is shown. Cannula assembly 418 comprises a cannula 414 which includes an internal shelf 618 notched or lanced toward its distal end, and a cannula housing 421 which includes stopcock assembly 582, seal member 606 and stabilizer plate 608. A proximally directed extension arm 766 is formed from the rearward portion of cannula housing 421. An aperture 768 is formed in extension arm 766. A proximally directed ledge 770 extends from stabilizer plate 608.

Figure 17:
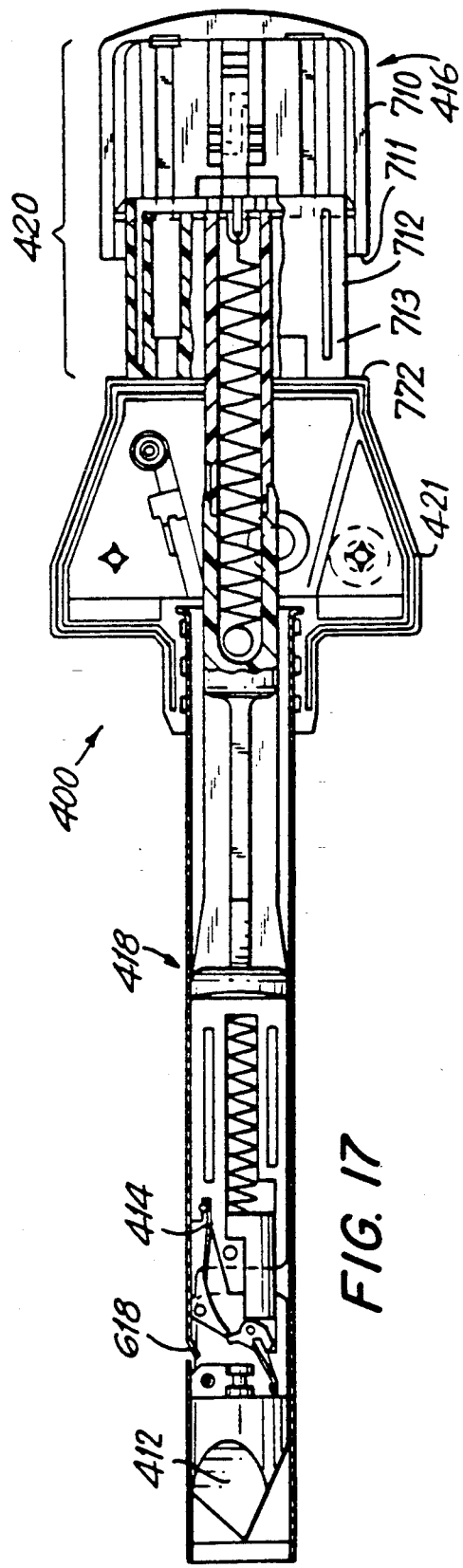
FIG. 17 is a sectional side view of the alternate trocar embodiment with the trocar tip in its retracted position.

In use, the endoscopic portion of trocar assembly 416 is inserted into cannula assembly 418 of trocar 400, as shown in FIG. 17. Insertion continues until front face 713 of inner housing 712 contacts rear face 772 of cannula housing 421. In this initial position, cutting tip 412 is within cannula 414, and inner housing 712 is distally extended from outer housing 710 with compression springs 714 unloaded. Obturator pusher arm 746 abuts finger 744 of obturator flange 742 under the bias of torsion spring 764. Spring 500 is also unloaded.

When the surgeon is ready to use trocar 400, cutting tip 412 is advanced from cannula 414 by compressing outer housing 710 toward cannula housing 421, e.g., through a palming action. This compression causes inner housing 712 to slide within outer housing 710 through cooperation between guide rails 722 and guide tracks 724, thereby loading compression springs 714. Distal motion of outer housing 710 relative to inner housing 712 and cannula housing 421 causes obturator 478 and cutting tip 412 to distally advance, thereby exposing cutting tip 412 from cannula 414. Distal advancement of obturator 478 is accomplished through contact between pusher arm 746, which is pivotally fixed to outer housing 710 by pin 732, and flange 742, which is fixedly secured to obturator 478. Distal movement of obturator 478 and cutting tip 412 loads spring 500.

Continued compression of outer housing 710 toward cannula housing 421 by the surgeon brings front face 711 of outer housing 710 into close proximity with rear face 722 of cannula housing 710. At this point, latch finger 752 is initially biased counterclockwise through contact of cam surface 758 with the front face of extension arm 766. Additional distal movement of outer housing 710 allows latch finger 752 to return clockwise under the bias of torsion spring 764 which results in hook 754 entering aperture 768. Thus, interaction between hook 754 and extension arm 766 locks trocar housing 420 to cannula housing 421, against the bias of springs 714.

As outer housing 710 moves into close proximity with cannula housing 421, two further mechanical interactions occur. First, the latch/pawl mechanism at the distal end of trocar assembly 416 functions to bring latch 510 into engagement with internal shelf 618, as described for trocar 10 hereinabove. Second, inclined cam surface 750 of pusher arm 746 contacts ledge 770 which extends proximally from stabilizer plate 608. This contact causes pusher arm 746 to pivot clockwise against the bias of torsion spring 764 and brings abutment face 748 out of engagement with finger 744 of flange 742. Thus, only interaction between latch 510 and internal shelf 618 prevents obturator 478 and cutting tip 412 from springing proximally under the force of loaded spring 500.

Figure 12:
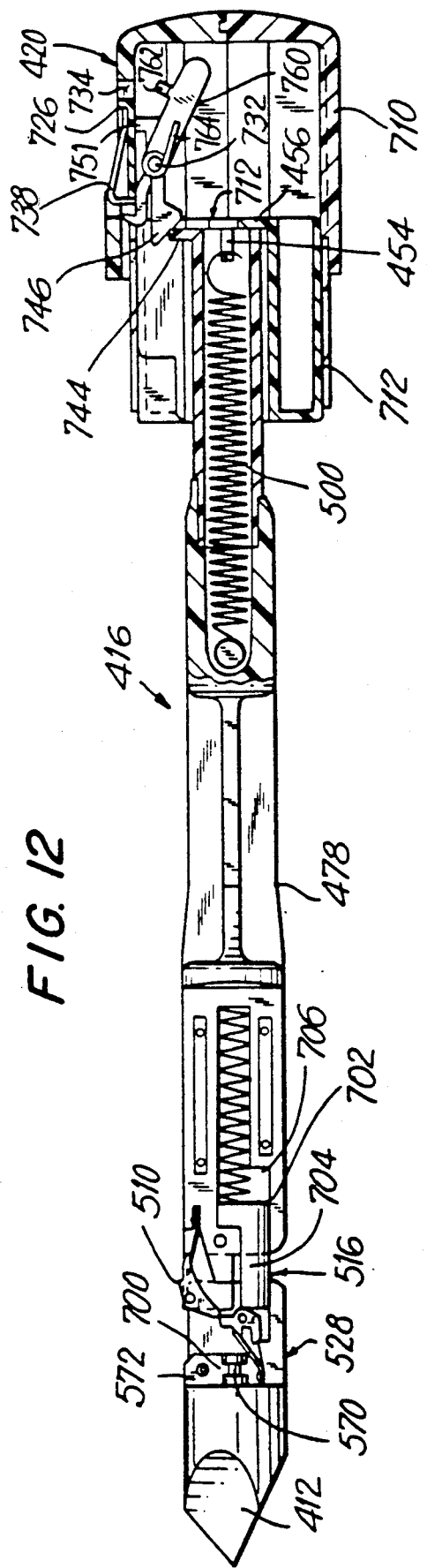
FIG. 12 is a sectional side view of an alternate embodiment of the trocar assembly of the present invention.

The trocar tip 412 is now armed and the surgeon may now press trocar 400 against a body wall, thereby causing the latch/pawl mechanism to function as described for trocar 10. Once the body cavity is entered by cutting tip 412, thereby removing all counterforce from cutting tip 412, obturator 478 and cutting tip spring proximally under the force of spring 500. As obturator 478 and fixedly secured flange 742 move proximally, pusher arm 746 remains pivoted atop ledge 770. Therefore, finger 744 moves proximally within inner housing 712 and contacts inclined face 760 on latch finger 752, thereby pivoting latch finger 752 counterclockwise against the bias of torsion spring 764. Hook 754 is thus released from engagement with aperture 768 in extension arm 766, thereby releasing outer housing 710 to move proximally with respect to inner housing 712 under the force of springs 714. Pusher arm 746 is thereby removed from ledge 770 and cams back over finger 744 to its initial proximal position with respect to finger 744, as shown in FIGS. 12 and 15. Trocar 400 is thus in condition to be rearmed, if so desired by the surgeon.

The surgeon may determine that it is desirable to manually disarm trocar 400 after cutting tip 412 has been advanced from cannula 414. In such case, release leaf spring 738 may be pressed by the surgeon. Release leaf spring 738 rests against latch finger 752 such that counterclockwise rotation of leaf spring 738 causes counterclockwise rotation of latch finger 752 around pin 732. Such counterclockwise movement of latch finger 752 releases hook 754 from aperture 768 in extension arm 766. Thus, outer housing 710 is free to move proximally with respect to inner housing 712 under the force of springs 714. Cutting tip 412 may then be manually retracted by rotating trocar housing 420 with respect to cannula housing 421, thereby removing latch 510 from internal shelf 618 which allows obturator 748 and cutting tip 412 to move proximally under the force of spring 500. Indicator tab 762 provides a visual indication to the surgeon of the position of cutting tip 412 relative to cannula 414 through viewing window 734.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention. For example, a variety of cutting tip configurations may be employed with the trocar of the invention, e.g., conical tips, dome tips, fluted tips, etc. Additional changes and modifications will be apparent to those of ordinary skill.

I claim:

1. A trocar comprising:

(a) A cannula assembly comprising a cannula and a cannula housing defining an internal cannula passage;

(b) a trocar assembly adapted to cooperate with said cannula assembly, said trocar assembly comprising a sharp trocar tip, an obturator shaft, and a trocar housing, said trocar tip and at least a portion of said obturator shaft being configured and dimensioned for entry into said internal cannula passage;

(c) releasable obturator means associated with the obturator shaft which releasably maintains the trocar tip in an extended position relative to said cannula;

(d) means for releasing the releasable obturator means; and (e) biasing means for retracting the trocar tip from said extended position to a retracted position in response to release of the releasable obturator means.

2. The trocar of claim 1, wherein said cannula is lanced or notched to form an internal shelf and said internal shelf is adapted to cooperate with said releasable obturator means to maintain said trocar tip in said first extended position.

3. The trocar of claim 1, wherein said releasable obturator means comprises a latch and a spring biasing said latch radially outward.

4. The trocar of claim 1, wherein said means for releasing the obturator means comprises a pawl.

5. The trocar of claim 4, wherein said trocar tip is mounted to an extension member, said extension member is reciprocally mounted to said obturator shaft, and said pawl is mounted to said extension member.

6. The trocar of claim 1, wherein said trocar assembly further comprises an extension member and said trocar tip is mounted to said extension member.

7. The trocar of claim 6, wherein said extension member is reciprocally mounted to said obturator shaft and is spring-biased away from said obturator shaft.

8. The trocar of claim 7, wherein said releasable obturator means maintains said trocar tip in a first extended position in which said extension member is in a spaced relation with respect to said obturator shaft and a second extended position in which said extension member is proximate said obturator shaft.

9. The trocar of claim 8, wherein said extension member assumes said second extended position in response to a counterforce being applied to said trocar tip.

10. The trocar of claim 8, wherein said means for releasing said releasable obturator means effects said release from said second extended position.

11. The trocar of claim 10, wherein said means for releasing said releasable obturator means comprises a pawl and said pawl releases said releasable obturator means when said extension member moves away from said proximate position relative to said obturator shaft.

12. The trocar of claim 1, wherein said trocar assembly further comprises an indicator means which signals the position of said trocar tip.

13. The trocar of claim 1, wherein said means for releasing the releasable obturator means and said biasing means automatically retract said trocar tip to said retracted position in response to removal of a counterforce from said trocar tip.

14. The trocar of claim 1, further comprising means for manually effecting retraction of said trocar tip from said extended position to said retracted position.

15. A trocar comprising:

(a) a cannula assembly comprising a cannula and a cannula housing defining an internal cannula passage;

(b) a trocar assembly adapted to cooperate with said cannula assembly, said trocar assembly comprising a sharp trocar tip, an obturator shaft, an outer trocar housing and an inner trocar housing, said inner trocar housing and outer trocar housing being reciprocally mounted to each other, and said trocar tip and at least a portion of said obturator shaft being configured and dimensioned for entry into said internal cannula passage;

(c) releasable obturator means associated with the obturator shaft which releasably maintains the trocar tip in a first extended position relative to said cannula;

(d) means for releasing the releasable obturator means; and (e) biasing means for retracting the trocar tip to a second retracted position in response to release of the releasable obturator means.

16. The trocar of claim 15, wherein said inner trocar housing and outer trocar tip housing are in relation when said trocar is in said retracted position, and wherein approximation of said inner and outer trocar housings moves said trocar tip into said extended position.

17. The trocar of claim 15, further comprising means for manually effecting retraction of said trocar tip from said extended position to said retracted position.

18. A method for inserting a trocar, comprising:

(a) advancing an obturator and a trocar tip to expose said trocar tip from a cannula, said trocar tip being maintained in said exposed position by means associated with said obturator;

(b) pressing said trocar tip against a body wall, said body wall thereby exerting a counterforce against said trocar tip;

(c) entering said trocar tip into a body cavity, thereby removing said counterforce form said trocar tip and actuating release means associated with said obturator shaft to release said maintaining means, whereby said trocar tip is automatically withdrawn into said cannula under the action of a biasing means.

19. The method of claim 18, wherein said maintaining means comprises a latch adapted to cooperate with a shelf lanced or notched into said cannula.

20. The method of claim 18, wherein said release means comprises a pawl adapted to contact and release said maintaining means.

* * * * *

UNITED STATES PATENT AND TRADEMARK OFFICE
CERTIFICATE OF CORRECTION

PATENT NO. : 5,116,353
DATED : May 26, 1992
INVENTOR(S) : Green

It is certified that error appears in the above—identified patent and that said Letters Patent is hereby corrected as shown below:

Column 5, line 9, after "arm" insert --88--; and
line 26, after "channel" insert --94--.

Column 6, line 4, after "spring" insert --188--; and
line 42, change "therwith" to --therewith--.

Column 10, line 21, after "cutting tip" insert --412--.

Claim 1, line 2, change "A" to --a--.

Claim 16, line 2, after "trocar" delete "tip",
after "in" insert --spaced--;
line 3, after "trocar" insert --tip--.

Claim 18, line 10, change "form" to --from--.

Signed and Sealed this

Nineteenth Day of October, 1993

Attest:

BRUCE LEHMAN

Attesting Officer

Commissioner of Patents and Trademarks

REEXAMINATION CERTIFICATE (2993rd)

United States Patent [19]

Green

[11] B1 5,116,353

[45] Certificate Issued Sep. 10, 1996

[54] SAFETY TROCAR

[75] Inventor: David T. Green, Westport, Conn.

[73] Assignee: Digital Voice Systems, Inc., Cambridge, Mass.

Reexamination Request:
No. 90/003,466, Jun. 13, 1994

Reexamination Certificate for:
Patent No.: 5,116,353
Issued: May 26, 1992
Appl. No.: 593,676
Filed: Oct. 5, 1990

[51] Int. Cl.[6] ............................................. A61B 17/32
[52] U.S. Cl. ........................ 606/184; 604/164; 30/366

[56] References Cited

U.S. PATENT DOCUMENTS

| | | |
|---|---|---|
| 1,248,492 | 12/1917 | Hill . |
| 1,640,311 | 8/1927 | Dawes . |
| 2,623,521 | 12/1952 | Shaw . |
| 4,094,217 | 6/1978 | Exline . |
| 4,256,119 | 3/1981 | Gauthier . |
| 4,527,561 | 7/1985 | Burns . |
| 4,535,773 | 8/1985 | Yoon . |
| 4,747,831 | 5/1988 | Kulli . |
| 4,767,413 | 8/1988 | Haber et al. . |
| 4,813,426 | 3/1989 | Haber et al. . |
| 4,817,631 | 4/1989 | Schnepp-Pesch et al. . |
| 4,874,382 | 10/1989 | Lindermann et al. . |
| 4,904,242 | 2/1990 | Kulli . |
| 4,946,446 | 8/1990 | Vadher . |
| 4,973,316 | 11/1990 | Dysarz . |
| 5,046,508 | 9/1991 | Weissler . |
| 5,066,288 | 11/1991 | Deniega et al. . |

OTHER PUBLICATIONS

"Needle For The Puncture And Lavage Of The Abdominal Cavity" by F. S. Zubairov.

*Primary Examiner*—Stephen C. Pellegrino

[57] ABSTRACT

A safety trocar is provided in which the cutting tip is withdrawn into the cannula in response to counterforce being removed from the cutting tip, e.g., by the tip entering a body cavity. The cutting tip is maintained in the exposed positioned by a mechanism associated with the oburator shaft, and is automatically withdrawn into the cannula under the force of a spring when the first mechanism is released by a second mechanism associated with the oburator. Penetration force is maintained at a minimum and safe and efficacious trocar entry is facilitated.

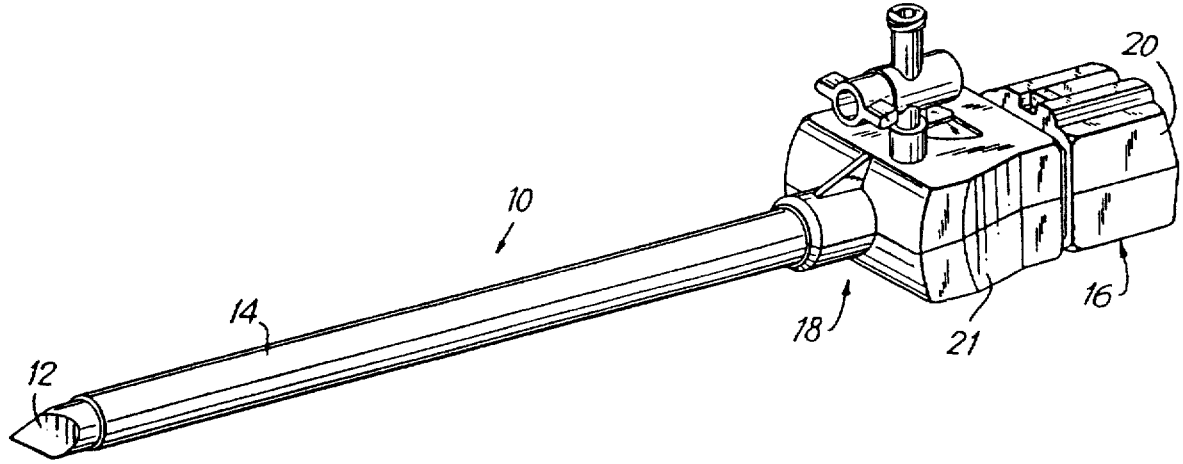

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15, 16 and 17 is confirmed.

Claims 1, 4, 10, 11, 13, 18 and 20 are determined to be patentable as amended.

Claims 2, 3, 5–9, 12, 14, and 19, dependent on an amended claim, are determined to be patentable.

New claims 21–25 are added and determined to be patentable.

1. A trocar comprising:
   (a) a cannula assembly comprising a cannula and a cannula housing defining an internal cannula passage;
   (b) a trocar assembly adapted to cooperate with said cannula assembly, said trocar assembly comprising a sharp trocar tip, an obturator shaft, and a trocar housing, said trocar tip and at least a portion of said obturator shaft being configured and dimensioned for entry into said internal cannula passage;
   (c) releasable obturator means [associated with] *mounted to* the obturator shaft which releasably maintains the trocar tip in an extended position relative to said cannula;
   (d) *pawl* means for releasing the releasable obturator means, *said pawl means being mounted to said trocar assembly for rotational movement with respect to said releasable obturator means;* and
   (e) biasing means for retracting the trocar tip from said extended position to a retracted position in response to release of the releasable obturator means.

4. The trocar of claim 1, wherein said *pawl* means for releasing the obturator means comprises a pawl.

10. The trocar of claim 8, wherein said *pawl* means for releasing said releasable obturator means effects said release from said second extended position.

11. The trocar of claim 10, herein said *pawl* means for releasing said releasable obturator means comprises a pawl and said pawl releases said releasable obturator means when said extension member moves away from said proximate position relative to said obturator shaft.

13. The trocar of claim 1, wherein said *pawl* means for releasing the releasable obturator means and said biasing means automatically retract said trocar tip to said retracted position in response to removal of a counterforce from said trocar tip.

18. A method for inserting a trocar, comprising:
   (a) advancing an obturator and a trocar tip to expose said trocar tip from a cannula, said trocar tip being maintained in said exposed position by means associated with said obturator;
   (b) pressing said trocar tip against a body wall, said body wall thereby exerting a counterforce against said trocar tip;
   (c) entering said trocar tip into a body cavity, thereby removing said counterforce from said trocar tip and actuating *pawl* release means [associated with said obturator shaft] *mounted to said obturator for rotational movement with respect to said maintaining means* to release said maintaining means, whereby said trocar tip is automatically withdrawn into said cannula under the action of a biasing means.

20. The method of claim 18, wherein said *pawl* release means comprises a pawl adapted to contact and release said maintaining means.

21. A trocar comprising:
   (a) a cannula assembly comprising a cannula and a cannula housing defining an internal cannula passage;
   (b) a trocar assembly adapted to cooperate with said cannula assembly, said trocar assembly comprising a sharp trocar tip, an obturator shaft, and a trocar housing, said trocar tip and at least a portion of said obturator shaft being configured and dimensioned for entry into said internal cannula passage;
   (c) latch means mounted to the obturator shaft which releasably maintains the trocar tip in an extended position relative to said cannula;
   (d) latch release means mounted to the trocar assembly for releasing the latch means, wherein movement of said trocar tip with respect to said trocar housing causes movement of said latch release means with respect to said trocar housing; and
   (e) biasing means for retracting the trocar tip from said extended position to a retracted position in response to release of the releasable obturator means.

22. The trocar of claim 21, wherein said latch release means is rotatably mounted to said trocar assembly.

23. A trocar comprising:
   (a) a cannula assembly comprising a cannula and a cannula housing defining an internal cannula passage;
   (b) a trocar assembly adapted to cooperate with said cannula assembly, said trocar assembly comprising a sharp trocar tip, an obturator shaft, and a trocar housing, said trocar tip and at least a portion of said obturator shaft being configured and dimensioned for entry into said internal cannula passage;
   (c) latch means mounted to the obturator shaft which releasably maintains the trocar tip in an extended position relative to said cannula;
   (d) latch release means mounted to the trocar assembly for releasing the latch means, wherein axial movement of said trocar tip with respect to said trocar housing causes concomitant axial movement of said latch release means with respect to said trocar housing; and
   (e) biasing means for retracting the trocar tip from said extended position to a retracted position in response to release of the releasable obturator means.

24. The trocar of claim 23, wherein said latch release means is rotatably mounted to said trocar assembly.

25. A trocar comprising:

(a) a cannula assembly comprising a cannula and a cannula housing defining an internal cannula passage;

(b) a trocar assembly adapted to cooperate with said cannula assembly, said trocar assembly comprising a sharp trocar tip, an obturator shaft, and a trocar housing, said trocar tip and at least a portion of said obturator shaft being configured and dimensioned for entry into said internal cannula passage;

(c) releasable obturator means mounted to the obturator shaft which releasably maintains the trocar tip in an extended position relative to said cannula;

(d) pawl means pivotally mounted to said trocar assembly for releasing the releasable obturator means; and (e) biasing means for retracting the trocar tip from said extended position to a retracted position in response to release of the releasable obturator means.

* * * * *